United States Patent
Torres Russo et al.

(10) Patent No.: US 6,743,949 B2
(45) Date of Patent: Jun. 1, 2004

(54) PROCESS OF OBTAINMENT OF RACEMIC CETAMINE ENANTIOMERS; PROCESS OF OBTAINMENT OF PHARMACEUTICALLY ACCEPTABLE SALTS FROM RACEMIC CETAMINE ENANTIOMES AND USE OF PHARMACEUTICALLY ACCEPTABLE SALTS OBTAINED BY MEANS OF SAID MENTIONED PROCESS

(75) Inventors: Valter Freire Torres Russo, Itapira (BR); Elisa Mannochio de Souza Russo, Itapira (BR)

(73) Assignee: Cristália Produtos Químicos e Farmacêuticos Ltda., Sao Paulo (BR)

( * ) Notice: Subject to any disclaimer, the term of this patent is extended or adjusted under 35 U.S.C. 154(b) by 0 days.

(21) Appl. No.: 10/297,815

(22) PCT Filed: Jun. 18, 2001

(86) PCT No.: PCT/BR01/00075

§ 371 (c)(1),
(2), (4) Date: Dec. 10, 2002

(87) PCT Pub. No.: WO01/98265

PCT Pub. Date: Dec. 27, 2001

(65) Prior Publication Data

US 2003/0212143 A1 Nov. 13, 2003

(30) Foreign Application Priority Data

Jun. 19, 2000 (BR) ............................................. 0002693

(51) Int. Cl.$^7$ ..................... C07C 225/18; A61K 31/137
(52) U.S. Cl. ....................................... 564/438; 564/307
(58) Field of Search ................................ 564/307, 438

(56) References Cited

U.S. PATENT DOCUMENTS 6,040,479 A * 3/2000 Steiner et al. .............. 564/304

FOREIGN PATENT DOCUMENTS

WO     WO 96/11894 A1    4/1996

* cited by examiner

*Primary Examiner*—Brian Davis
(74) *Attorney, Agent, or Firm*—Birch, Stewart, Kolasch & Birch, LLP

(57) ABSTRACT

The present invention describes a new process for obtainment of the cetamine enantiomers, from the racemic cetamine resolution with the aid of an agent of chiral resolution, which provides the selective crystallization of its enantiomers. The resolution agent is employed in special concentration conditions, which provides stability, reproducibility and high enantiomeric purity to the precipitated diasteromer salt, making feasible the industrial production of the S-cetamine and its pharmaceutically acceptable salts.

13 Claims, No Drawings

PROCESS OF OBTAINMENT OF RACEMIC CETAMINE ENANTIOMERS; PROCESS OF OBTAINMENT OF PHARMACEUTICALLY ACCEPTABLE SALTS FROM RACEMIC CETAMINE ENANTIOMES AND USE OF PHARMACEUTICALLY ACCEPTABLE SALTS OBTAINED BY MEANS OF SAID MENTIONED PROCESS

This application is the national phase under 35 U.S.C. § 371 of PCT International Application No. PCT/BR01/00075 which has an International filing date of Jun. 18, 2001, which designated the United States of America.

The present invention refers to a new process for obtaining S-cetamine from racemic cetamine, by means of procedures of selective crystallization of its enantiomers with the aid of a chiral resolution agent employed in special concentration conditions, which confer stability and reproducibility on the precipitation of tartrate salts.

The (R,S)-2-(2-chlorophenyl)-2-methylamin cyclohexanone is known in Brazil with the generic name of cetamine.

Cetamine is a drug with sedative, analgesic and anesthesic properties, which molecular structure presents a chiral center (asymmetric carbon), thus having two enantiomers, known as S-cetamine and R-cetamine,

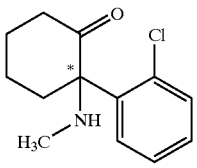

FIG. 1: Molecular formula of cetamine, with the representation of its asymmetric carbon.

Since it was introduced in the market, more than 20 years ago, it is commercialized in its racemic form, which consists of a mix in equal proportions of both enantiomers.

The last ten years of development of new drugs were marked by a deep change in the comprehension of the activity associated to the special molecular structure of new molecules and their receivers within the organism.

The three-dimension mapping of several specific receivers and enzymes, revealed the importance of development of enantiomeric defined drugs, as the different enantiomers of a given substance present differences on distribution of their ligands at three-dimension level. This different distribution of these ligands can provide different degrees of complementarity between these enantiomers and the activity sites.

In the cases where one of the enantiomers presents a high degree of complementarity with the action site, it is named eutomer. The eutomer, when exerting this activity, usually interferes with the action of his antipode, the distomer.

The distomer, however, is not always a passive component in the biological environment. It can actuate as agonist, antagonist, and it can exert activity on other receivers, can produce undesirable side effects and can even exert an activity complementary to the activity exerted by eutomer. (Williams K, Lee E—Importance of Drug Enantiomers in Clinical Pharmacology—Drugs, 30: 333–354 (1985)).

The development of new drugs in this last ten years has practically postulated that in cases where distomer do not contribute to the overall effect of one drug, he can be considered as an undesirable impurity, because, as it is a different entity from its eutomer, he can be potentially toxic. (Sheldon RA—Chirotechnology—Industrial Synthesis of Optically Active Compounds—pg. 50 (1993)).

Among several other well known drugs, we can mention some examples where distomers present undesirable side effect, which are not characteristics of their eutomers: Penicilamine is an anti-arthritis agent, where eutomer is the S-isomer, and its distomer is the R-isomer, which is highly toxic (mutagenic); the S,S-etambulol presents tuberculostatic activity 200 times superior to its distomer (R,R-etambulol), which causes optic neuritis that can result in blindness; L-dopa, used to the Parkinson Disease, is commercialized in this form, as its distomer produces severe side effects, such as granulocytopenia; and certainly, the most remarkable example of a drug formerly commercialized in its racemic form presenting the distomer associated with severe side effects, is talidomide. Commercialized during the sixties, as sedative, from the two enantiomers present in it, R-talidomide is the one who is effectively sedative, while its distomer (S-talidomide) is highly teratogenic, causing severe abnormalities for the phoetus. (Sheldon RA—Chirotechnology—Industrial Synthesis of Optically Active Compounds, pg 53 (1993)).

These new concepts are reformulating the use of drugs developed and commercialized in the form of racemic mixtures, due the fact that, in ancient times, it is not known the complexity of the interaction of different enantiomers in biological environment.

Cetamine is one of these drugs developed prior to the clarification of this new concepts. Recently, researches discovered that side effects post-anesthesia seen with its use, among them hallucinations and restiveness, are mainly associated to its R-enantiomer, while its S-enantiomer (eutomer) is the effectively anesthesic one, exerting this activity with a power about three or four times higher to its distomer. (Puu G, Koch M, Artursson E—Biochemical Pharmacology, 41(12): 2043–2045(1991); Sheldon, R. A.—Chirotechnology—Industrial Synthesis of Optically Active Compounds, p. 53 (1993)).

Feasibility of commercialization of this pure enantiomer from cetamine, S-cetamine, depends on the development of processes industrially efficient for its obtainment.

Among the available references that present procedures of obtaining S-isomer from cetamine, we have the procedure described in the patent DE 2062620 (Hudyma T W, Holmes S W e Hooper I R, de 1971), in which the obtainment of the S-cetamine is effected from racemic cetamine by means of the procedure of resolution with acid L-(+)-tartaric. The reaction medium consists of acetone and water and a reagent, the base racemic cetamine and the tartaric acid are employed in equivalent amounts in mol. The diastereomer salt separated in this procedure is recrystallized twice from acetonitrile, the isolated basis (S-cetamine) is also recrystallized and its chloridrate also suffers a rechrystallization to finally present a high enantiomeric purity with a low overall yield.

The consecutive recrystallization to which the several intermediate products and the final product are submitted, show a low enantiomeric purity of the tartrate salt from S-cetamine initially separated.

Industrially, the use of this procedure presents some disadvantages, among them the extensive purifications due to the low enantiomeric purity of the S-cetamine tartrate initially separated during the resolution process. Another disadvantage is associated to the solvent used in the purification of this salt, which is the acetonitrile, a toxic solvent which use in high proportions is not recommended.

In addition to these factors, experimentally this procedure shows a great variation of the enantiomeric purity of the precipitated S-cetamine tartrate, which interferes directly on the purification procedures for this salt. In some cases, also, the procedure is not efficient to separate enantiomers, occurring the crystallization on both forms, i.e. the S-cetamine and the R-cetamine tartrates, in proportions almost equivalent. The success of the recrystallization in acetonitrile is directly dependent on the enantiomeric purity of the salt initially precipitated, which, when low, presents separation of the product in the form of oil, which crystallizes slowly, without effective increments of this enantiomeric purity, becoming an additional problem in the adequacy of the method to a industrial scale production.

The patent WO 97/43244 (Gangkafner S, Grunenwald J, Steiner K, de 1997) describes a procedure almost identic to the patent DE 2062620 mentioned above, where the author only replaces the recrystallization solvent of S-cetamine tartrate, acetonitrile, by a mix of acetone and water.

It describes also some variants effected for this procedure, changing solvents used, and also the use of the resolution agent in amounts not proportional to the racemic base cetamine molar equivalent, this resolution agent being used in amount superior to the molar equivalent amount of the base cetamine.

As in the above reference, this procedure presents large variations in the precipitated amounts and in the separated salt enantiomeric purity, the S-cetamine tartrate. Due to the low enantiomeric purity of the precipitated salt, the product of the optical resolution needs to undergo reprocessing via recrystallization, in order to reach a higher enantiomeric purity, and this recrystallization represents the addition of one more phase in the procedure of obtaining S-cetamine, increasing the cost for the productive process.

There is also the patent WO 95/08529 (Grover E R, Mazzeo J R, Merion M, Petersen J S, Schwartz M E, de 1995), where exotic chiral surfactant discovered by them and special equipment for the separation of the enantiomers of racemic cetamine are used. This patent presents its application aiming at the field of Analytic Chemistry, being its use in industrial conditions not practicable, in economic terms.

The patent WO 96/11894 (A' Campo CPG, Leloux M S, from 1996) describes a process for separation of enantiomers from racemic mixtures by means of procedure of extraction in countercurrent, using at least two substances, one of them being the liquid in which the racemic mixture to be separated is present and the other containing the chiral adjuvant, which is combined with a substance forming the gel in the form of discrete particles in a liquid separated from the flow counter-current liquid containing the racemate, to be separated by means of a microporous membrane of pores suitable to solution passage and not to gel passage.

The separation principle described in this patent is similar to the chromatography employed in liquid chromatography or separation methodology of simulated movable bed. The execution of these kinds of procedures at industrial level requires special industrial equipment, which are normally very complex and which cost is situated in the range of a million dollars for use in procedures requiring the production of hundreds of kilos/year. In accordance to what is described in this patent, after a complex procedure for treatment of the racemic mixture for the obtainment of S-isomer from cetamine, the results presented by the authors showed that in the best condition found for obtainment of S-cetamine, this latter is separated with enantiomeric excess of only 91%. Therefore, the product obtained has to be later processed for obtainment of S-cetamine with higher enantiomeric excess.

Analyzing the processes available until now for separating the S-isomer of cetamine, we can remark that they are divided of two types of methodologies:

1. Methods of separation for methodologies involving procedures related to the liquid chromatography;
2. Separation of racemic cetamine by means of selective crystallization with the aid of a resolution agent Procedures related to liquid chromatography usually involve the use of special equipment to effect the separation. In these cases, the amounts of solvents used are very high, being necessary auxiliary equipment for the concentration of these solvents and separation of the desired product. In addition of these initial disadvantage we can remark, as described in the patent WO 96/11894, that the product separated in the best case presents enantiomeric excess of 91%, and has to undergo later purification, in order to reach a higher enantiomeric excess.

On the other hand, procedures existing up to now, involving selected crystallization of the S-cetamine diastereomer, are presented as procedures of small efficiency due to the low and varied enantiomeric purity obtained in the starting phase. This low efficiency in this salt separation causes the need of effecting subsequent purifications procedure for this salt, which has mandatory to have their parameters (such as solvent amount, recrystallization number, etc.) set for each batch obtained, as these processes reveal to be unstable relating to the produced material, both quantitatively and qualitatively.

Stabilization of the initial phases of the S-cetamine tartrate, is shown to be the critical phase of this type of separation procedure, reflecting directly on the feasibility of industrial production of S-cetamine.

The present invention describes a new process, industrially efficient and economic for the obtainment of enantiomers from racemic cetamine.

The procedure described in the present invention consists in the separation of S-cetamine under the form of diastereomer salt by means of selective crystallization with the addition of acid L-(+)-tartaric as resolution agent. However, the procedure can also be effected with the use of its antipode, the acid D-(−)-tartaric presenting similar results, but occurring first the obtainment of the tartrate R-cetamine. Preferably, the process is effected with the acid L-(+)-tartaric, in order to precipitate the S-isomer initially.

Procedures described until now use the resolution and the cetamine in molar equivalent amount, or even the resolution agent is used in molar excess related to the basic cetamine.

We remark that the conditions used in these procedures of resolution described until now give instability to the process, which can be evidenced mainly by the large variation on the enantiomeric purity of the formed salt.

Resolution procedures via formation of diastereomers salt formation are made up by the obtainment of one of the enantiomers in its salt form with the resolution agent. Higher the separated enantiomer purity, more efficient the process, and smaller the number of subsequent purification phases. If enantiomeric purity of the separated enantiomer is very low, i.e., desired enantiomer presents a small enantiomeric excess relating to its antipode, more difficult is his purification and consequent enantiomeric enrichment.

We noticed that when we performed these resolution procedures using smaller amounts of the resolution agent, i.e., when we used racemic cetamine in its basic form with molar excess relating to the resolution agent, a remarkable process improvement is reached. As we mentioned before, procedures described until now are unstable as for regard to the yielding obtained from S-cetamine tartrate and also when the enantiomeric purity of this salt, which is variable and invariably low. Thanks to this low enantiomeric purity, the tartrate salt needs to be re-processed by means of recrystallization so that we can promote its enantiomeric enrichment, which is required for the obtainment of the S-cetamine chloridrate from the high enantiomeric excess.

Unlike previous procedures, the present invention describes a stable and efficient procedure, which yields a product with high enantiomeric purity, eliminating the need of precipitated salt recrystallization, as this salt is presented enantiomerically almost pure. Following this high enantiomeric purity, we also find the stabilization of the obtained yielding, which are shown to be high and constant. Raw S-cetamine tartrate obtained directly from the process, without the phase of recrystallization, in accordance with parameter described in this invention, presents a high enantiomeric purity, which represents a progress of the technique as compared with results obtained by processes previously described, as in these ones the desirable enantiomeric purity index is only obtained after the phase of recrystallization of this salt.

Another factor that presents a great influence on the obtaining of S-cetamine tartrate refers to the instability of the reaction medium seen on the procedure described previously to the present invention. The large variation of yielding followed by the variation of the precipitated tartrate enantiomeric purity is due to the instability of the reaction medium in the conditions proposed by the other authors. This instability makes the procedure quantitatively and qualitatively little reproductive.

Selective crystallization procedures for diastereomer salts require reaction media that are stable enough, so that factors such as agitation speed, or even different kind of agitation do not influence on the yielding obtained. Other factors that present much influence when the procedure is unstable, are those relating to the reaction times, system cooling speed, being these factors of complicated setting, mainly when procedures undergo scale amplifications, reaction equipment change and also variations in room temperature. The procedures described up to now present this type of behavior, which makes the process little solid in normal production conditions.

Procedure described in the present invention is sufficiently solid almost not to be influenced by all these described factors. Regardless of the reaction time, agitation speed, solvent and reagent amounts employed, types of agitation, the product obtained at the end of the process of selective crystallization presents a quantitative and qualitative yielding similar and proportional to the expected amounts for small scales or industrial scales. The end of crystallization process can be monitored by any usual analytic quantitative procedure on the reaction solvent, having as parameter the stabilization of the cetamine quantity present in this solvent.

In accordance with the present invention, selective crystallization of S-cetamine tartrate can be performed in various solvents, preferably in solvents miscible with water, such alcohols of $C_1$–$C_6$ chain, tetrahydrofuran and acetone. Mixtures of these solvents also have shown to be efficient, once adjusted to their conditions. Preferably, the used solvent is acetone.

The concentration of the reaction medium is also a factor that influences the separation of diastereomers, and on solvents mentioned above it can range from 0.10M (molar) to 1.0M, calculated in terms of racemic cetamine in basic form.

Water amount present in the process is also an important factor for help in the obtainment of the cetamine diastereomer salt, giving stability to the process, which can be seen together with obtained results. In our trials, we defined that the water amount to be present shall be within a range from 5.0% to 20% (v/v) relating to the solvent employed in the resolution process.

Resolution agent, preferably the acid L-(+)-tartaric (in order to precipitate primarily the S-cetamine tartrate), in accordance with the present invention, is used in proportions ranging from 0.25 equivalent molar to 0.8 equivalent molar, relating to 1.0 equivalent molar of racemic cetamine. The procedure also can be effected with the use of the acid D-(−)-tartaric in the same conditions, however the precipitation of the R-cetamine occurring first, and the S-cetamine shall be recovered from the solution.

In accordance with described parameters, the procedure of cetamine resolution consists of the dissolution of its basic form in one of the solvents or mixtures of solvent stipulated, under heating between 30 and 56° C., and later addition preferably of the acid L-(+)-tartaric, on previously stipulated proportions, in order to precipitate initially the S-cetamine tartrate. The water is added in described proportions and the reaction medium is maintained in an approximated temperature of 50 to 60° C. until complete dissolution of the solids. The time required for this dissolution shall depend on the amounts of reagents and solvents employed in the reaction, as well as on the efficiency of the heating system. However, in accordance with the previously described, these parameters do not present any influence on the process.

Once the solid is dissolved, the heating is turned off and the reaction medium is maintained in agitation until complete precipitation of the tartrate salt. Time required for the completion of this precipitation depends on the reagent and solvents amount employed, as well as on the system cooling speed. Due to the solidity process described, parameters such as agitation speed and cooling do not significantly influence on the quantitatively and qualitatively yielding of the tartrate salt, showing the high efficiency of this process.

To define that crystallization reached its end, any quantitative analytical methodology involving the analysis of reaction solvent can be employed, using as parameters the stabilization of cetamine concentration present in this reaction solvent.

The precipitated S-cetamine tartrate salt is separated from reaction medium by means of filtration, centrifugation or any proper solid-liquid separation technique. This solid is agitated with the same solvent initially employed, with an approximated ratio of 1/20 to 1/2 (mass/mass) respectively. This solid is once more separated by filtration, centrifugation or any other usual solid-liquid separation technique.

As we mentioned before, this raw tartrate obtained directly from the process presents high enantiomeric purity, being equivalent to the enantiomeric purity, obtained by procedures existing up to now only after the recrystallization phase. This high enantiomeric purity shows the efficiency of the process described in the present invention to the obtainment of the tartrate salt directly from the reaction medium.

Once separated the S-cetamine tartrate, this is dissolved on water in order to get a solution, with concentration not higher than 20%. The basis is then obtained by means of the addition of an alkaline solution to this medium, adjusting pH between 9 and 12. In these conditions occurs the base precipitation that can be separated from the reaction medium by means of any usual procedure of liquid-solid separation. Alternatively, the base can be extracted with organic solvents not miscible in water, from the aqueous tartrate solution, by addition of alkaline solution, organic solvent separated and later evaporated for the obtaining of S-cetamine in its basic form.

Among the bases that can be used to S-cetamine separation are the hydroxides, carbonates and bicarbonates, preferably the sodium, potassium and ammonium. The amount control of the solution to be added is effected by means of the pH of final solution, which shall be adjusted at a range between 9 and 12, which represents the ideal pH for the obtainment of S-cetamine base.

These alkaline solutions can be employed in several concentrations, ranging between 5% to 50% of the base in water, however, lower or higher concentration can also be used.

Usually S-cetamine obtained in its raw state, directly from its procedure for obtainment from its salt, present enantiomeric excess higher than 95%. Its recrystallization can be effected from alcohols $C_1$–$C_6$, mixtures from these alcohol and water, alkanes $C_5$–$C_{12}$, cycloalkanes $C_5$–$C_{12}$, acetone, mixtures of acetone and water, in addition to mixtures among these solvents, to the obtainment with enantiomeric excess higher than 99%.

To the obtainment of the other cetamine anantiomer, solvent from reaction medium of S-cetamine tartrate crystallization is roto-evaporated until dry, yielding a solid that is dissolved in a solution of 0.1N to 3N of hydrochloric acid, employed in enough amount for its complete dissolution. The resulting solution is them treated in analog manner to the S-cetamine tartrate solution, via addition of alkaline solution for obtainment of the base and its purification to reach an enantiomeric excess higher than 99%, in accordance with the same parameter established for S-cetamine obtainment.

In a final phase, recrystallized S-cetamine is turned into a salt pharmaceutically acceptable, such as chloridrate, citrate, succinate, mesilate, besilate, among others.

The obtainment of the pharmaceutically acceptable S-cetamine salt can be effected in several ways to the skilled in the art adepts, as by dissolution in water miscible media and addition of proper acid concentrated or gaseous, or even in media not water-miscible, via addition of the proper acid in gaseous or concentrated form. Among the solvents which we can proceed to its preparation are $C_1$–$C_6$ alcohols, ethers, esters, cetones, chloroform, dichloremethane, aromatic solvents such as toluene, in addition to mixtures between these solvents which are employed in concentrations ranging from 5% to 50% of the base. Acid is added in amounts ranging from 1.0 to 10.0 molar equivalents relating to the base preferably ranging from 1.0 to 2.0 molar equivalents relating to the base.

Preferably, pharmaceutically acceptable salt is chloridrate, which is obtained from the basic form of the cetamine enantiomer, in accordance with parameters previously described.

Among solvents listed for the pharmaceutically acceptable salt obtainment from cetamine enantiomers, preferably methanol, ethanol, propanol, isopropanol, mixture of these alcohols with water, acetone, acetone mixed in water, methyl isobutyl cetone, diethyl ether, methyl, methyl terc-butyl ether, chloroform, dichloromethane, toluene and mixtures among these solvents are used.

Yielding reached by this process are around 70% in real yielding of S-cetamine in its basic form with enantiomeric excess higher than 99%, i.e. by means of the described process in the present invention, we obtain at the same time a high S-cetamine yielding, and a high enantiomeric purity, by means of a much more economic and feasible procedure, due to the elimination of the phase, previously required, of successive crystallization of S-cetamine tartrate of low enantiomeric purity separated in accordance with procedures previously described. In addition to these required recrystallization being extra phases for obtainment of purified salt, they contribute for the decrease of overall yielding of S-cetamine.

Process described also provides the stabilization of precipitated salt amounts, eliminating the need of effecting different purification procedures each time that S-cetamine tartrate is precipitated.

Factors that usually interfere on this procedures of diastereomers salt separation, as agitation speed and time required to the precipitation, were exhaustively tested and showed practically not interfere on yielding reached and on precipitated salt quality, showing that the procedure presents enough stability and sturdiness to be industrially executed.

Pharmaceutically acceptable S-cetamine salts, preferably the S-cetamine chloridrate, can be employed for preparation of pharmaceutic compositions to be employed in Medicine and Veterinary, in analogies to exhausting pharmaceutical compositions to racemic cetamine, as well as in new formulations, in the sense of obtained anesthesic/analgesic compositions presenting differentiate properties and with smaller side effects.

Experimental part described below is made up of illustrative examples, but not exhaustive ones, about obtainment of racemic cetamine enantiomers, showing in general lines, the higher efficiency of this procedure over the others proposed up to now.

The following examples illustrate the cetamines enantiomers obtainment:

EXAMPLE 1

Precipitation of S-Cetamine Tartrate

In a reactor with heating and agitation were added 475.5 g (2.0 mol) of racemic base cetamine and 6 liters of acetone. Under constant agitation, the mixture was heated until solid dissolution. 180 g (1.2 mol) of acid L-(+)-tartaric and 0.4 liters of water were added. The reaction medium was leaded to the reflux and heating maintained until complete dissolution of acid and then turned off. The limpid and colorless solution was maintained under stirring during about 12 hours. Precipitated solid was separated by filtration and placed in a container with agitation. 1.5 liters of acetone were added and the mixed remained under agitation for one hour. The solid was filtered and dry in a stove up to constant weight.

Yielding: m=344.5 g $[\alpha]^D_{25}$=+68.8° (c=2, $H_2O$)

MP=178–180° C.

EXAMPLE 2

Recrystallization of S-Cetamine Tartrate 2 g of S-cetamine tartrate obtained during procedure described on example 1 were recrystallized from a solution containing 40 mL of acetone and 2.7 mL of water. Solid obtained was filtered, yielding 1.4 g of S-cetamine with melting point and specific rotation unchanged relating to the product obtained in example 1.

EXAMPLE 3

Obtainment of Base S-Cetamine 340 g of S-cetamine tartrate, obtained in accordance with procedure described on example 1 were directly dissolved in 2.9 liters of water and 2.9 liters of ether were added. The aqueous phase pH was set in 12 with addition of NaOH 30% solution. Etheric phase was separated and washed with water and dried with anhydride sodium sulfate. Ether was them roto-evaporated until dry and the solid (base S-cetamine) dried in stove until constant weight.

Yielding m=182 g $[\alpha]^D_{25}$=−56.9° (c=2, EtOH)

MP=120–122° C.

EXAMPLE 4

Recrystallization of Base S-Cetamine 180 g of the product obtained in example 2 were recrystallized from 6 L of hexane, yielding 168 g of base S-cetamine, MP=120–122° C., $[\alpha]^D_{25}$=−57.8° (c=2, EtOH) (theoretical yielding of 72% over the initial racemic basic cetamine).

EXAMPLE 5

Obtainment of S-Cetamine Chloridrate 165 g of product obtained in example 3 was dissolved in 4.5 liters of ethanol 96°. This solution was saturated with HCl gas and cooled to 15° C. 4.6 liters of ethyl ether were added and the reaction medium was maintained under agitation for 1 hour. The solid obtained was filtered and reserved. The solution was again cooled, saturated with HCl and maintained under agitation for 1 more hour. Solids were put together, agitated with 2 liters of the absolute ethanol; ether (1:1) for half an hour. The S-cetamine chloridrate was filtered and dried on stove until constant weight.

Yielding: m=172 g
$[\alpha]^P{}_{25}$=+92.6° (c=2, H$_2$O)
PF=275–278° C.
ee (HPLC)>99.5%

EXAMPLE 6

Obtaining of the Raw Basis R-Cetamine

Acetone from example 1 were put together and evaporated until dry, yielding a white solid. A 20 g sample of this solid was dissolved in 200 mL of a HCl 1.0N solution under agitation. Once dissolved, pH of solution was raised to 12 with the addition of concentrated ammonium hydroxide. The precipitated solid was filtered, washed with water and dried in stove until constant weight.

Yielding m=17.2 g
MP=110–118° C.

EXAMPLE 7

Obtainment of Pure Base R-Cetamine 17 g of raw R-cetamine obtained in accordance with the procedure described on example 6, are recrystallized from 580 ml of hexane, yielding the pure base R-cetamine.

Yielding m=12.6 g
MP=119–121° C.
$[\alpha]^P{}_{25}$=+57.6° (c=2, EtOH)

EXAMPLE 8

Obtaining of R-Cetamine Chloridrate 11.0 g of R-cetamine pure base, obtained in accordance to the procedure shown in Example 7, are transformed in R-cetamine chloridrate following the procedure described on Example 5, the amounts employed of sovents being corrected.

Yielding: m=11.2 g
$[\alpha]^P{}_{25}$=−92.4° (c=2, H$_2$O)

With the purpose of checking the influence of the resolution agent amount of the resolution agent, relating to the base racemic cetamine, we performed several tests, which results are presented in Table 1. In each one of the tests 23.78 g (0.1 mol) of racemic base cetamine in 300 mL of acetone were added. The mixture was heated until de solid dissolution, and the described amount of the resolution agent was added followed by 20 mL of water. The solution was reflowed until complete dissolution of the resolution agent. After that, heating was removed and the solution maintained under stirring for about 12 hours. The precipitated solid was filtered, washed with 75 mL of acetone and dried in stove and its mass was weighed.

This solid was dissolved in water and the raw base cetamine was precipitated directly from this addition medium, with addition of concentrated NH$_4$OH. Solid was filtered, washed with water and had its specific rotation measured in order to check the efficiency of separation phase of diastomer salt.

Tabled results correspond to the data obtained from a series of five experiences for each different amount of the resolution agent used, relating to the fixed amount of racemic base cetamine.

TABLE 1

Influence of the amount of resolution agent on the enantiomeric purity of the isolated raw s-cetamine.

| Tests | Amounts of resolution agent | Raw tartarate mass | Base specific Rotation |
|---|---|---|---|
| 1 | 15.01 g (0.1 mol) | 25 g a 33 g* | min. −20°* |
| 2 | 12.0 g (0.08 mol) | 23 g a 29.7 g | min. −41° |
| 3 | 11.26 g (0.075 mol) | 22 g a 25 g | min. −49° |
| 5 | 10.51 g (0.07 mol) | 22 g a 24 g | min. −52° |
| 5 | 9.0 g (0.06 mol) | 16 g a 20 g | min. −55° |
| 6 | 7.5 g (0.05 mol) | 15 g a 17 g | min. −55° |
| 7 | 6.0 g (0.04 mol) | 10 g a 13 g | min. −55° |
| 8 | 4.5 g (0.03 mol) | 8 g a 11 g | min. −56° |
| 9 | 3.75 g (0.025 mol) | 4.0 g a 5.3 g | min. −57° |
| 10 | 3.0 g (0.02 mol) | 3.2 g a 4.6 g | min. −57° |

*Product presents large variation for the enantiomeric purity of the respective isolated base.

In accordance with the presented results, we can conclude that the trials effected with equivalent amounts in mol of base racemic cetamine and tartaric acid, influence in a negative way on the procedure, adding instability to the process which presents variable yielding in mass, being followed by a wide variation in the specific rotations of the products obtained, showing the low efficiency in cetamine resolution. However, in the subsequent tests, these variations are not seen, showing that the use of he resolution agent in the proposed amounts in the present invention adds stability to the process, in addition to provide the obtainment of high enantiomeric purity in its raw state, without the need of later purification of this salt.

What is claimed is:

1. A process for producing ketamine enantiomers comprising the steps of:
   a) preparing a solution of racemic ketamine in an organic solvent in a concentration ranging from 0.1M to 1.0M of ketamine;
   b) adding a resolution agent in an amount ranging from 0.25 to 0.80 molar equivalent in relation to ketamine base;
   c) adding water in an amount ranging from 5% to 20% in relation to the organic solvent;
   d) dissolving all solids by heating;
   e) separating one diastereomeric salt of one ketamine enantiomer by solid-liquid separation procedures selected from filtration, centrifugation, and decantation;
   f) dissolving the diastereomeric salt of ketamine in water in order to obtain a concentration not higher than 20% of the ketamine diastereomeric salt;
   g) adding an alkaline solution to reach a pH ranging from 9 to 12 to precipitate the ketamine enantiomer;
   h) purifying the ketamine enantiomer by crystallization using a solvent selected from the group consisting of $C_1$–$C_6$ alcohols, $C_5$–$C_{12}$ alkanes, $C_5$–$C_{12}$ cycloalkanes, acetone, or mixtures thereof;
   i) evaporating the remaining solvent from step (e) separating the other enantiomer;
   j) dissolving the resulting solid from step (i) in enough amount of a 0.1N to 3.0N hydrochloric acid solution, and proceeding as in steps (g) to (h) in order to separate the other ketamine enantiomer.

2. The process according to claim 1, wherein the organic solvent used in step (a) is a water-miscible solvent selected from the group consisting of $C_1$–$C_6$ alcohols, tetrahydrofuran, and acetone.

3. The process according to claim 2, wherein the organic solvent is acetone.

4. The process according to claim 1, wherein the resolution agent used in step (b) is selected from the enantiomers of tartaric acid.

5. The process according to claim 4, wherein the enantiomer of tartaric acid is the L-(+)-tartaric acid.

6. The process according to claim 4, wherein the enantiomer of tartaric acid is the D-(−)-tartaric acid.

7. The process according to claim 1, wherein the alkaline solution used in step (g) is selected from hydroxides, carbonates, and bicarbonates of sodium, potassium, or ammonium.

8. A process for producing pharmaceutically acceptable salts of ketamine enantiomers comprising the steps of:
 (i) dissolving ketamine enantiomer base in an organic solvent selected from the group consisting of $C_1$–$C_6$ alcohols, ethers, esters, ketones, chloroform, dichloromethane, and toluene, in a concentration ranging from 5% to 50%; and
 (ii) adding an acid in amounts ranging from 1.0 to 10.0 molar equivalents in relation to ketamine.

9. The process according to claim 8, wherein the pharmaceutically acceptable salt is the hydrochloride.

10. The process according to claim 8, wherein the organic solvent used in step (i) is selected from a group consisting of methanol, ethanol, isopropanol, mixtures of these alcohols with water, methyl isobutyl ketone, diethyl ether, methyl tert-butyl ether, chloroform, dichloromethane, toluene, and mixtures thereof.

11. The process according to claim 8, wherein the acid of step (ii) is used in an amount ranging from 1.0 to 2.0 molar equivalents in relation to ketamine.

12. A method of medical or veterinary anesthetic/analgesic treatment with fewer side effects characterized by using ketamine enantiomers, or their pharmaceutically acceptable salts, produced by the process of claim 1.

13. A method of medical or veterinary anesthetic/analgesic treatment with fewer side effects characterized by using ketamine enantiomers, or their pharmaceutically acceptable salts, produced by the process of claim 8.

* * * * *